United States Patent
Pflaum

(10) Patent No.: US 6,891,047 B2
(45) Date of Patent: May 10, 2005

(54) PROCESS FOR THE PREPARATION OF AMORPHOUS ATORVASTATIN

(75) Inventor: Zlatko Pflaum, Domzale (SI)

(73) Assignee: LEK Pharmaceuticals d.d., Ljubljana (SI)

( * ) Notice: Subject to any disclaimer, the term of this patent is extended or adjusted under 35 U.S.C. 154(b) by 0 days.

(21) Appl. No.: 10/614,534

(22) Filed: Jul. 7, 2003

(65) Prior Publication Data

US 2004/0024046 A1 Feb. 5, 2004

Related U.S. Application Data

(63) Continuation of application No. 10/149,348, filed as application No. PCT/IB00/01797 on Dec. 5, 2000, now Pat. No. 6,613,916.

(30) Foreign Application Priority Data

Dec. 10, 1999 (SI) .............................................. P-9900271

(51) Int. Cl.[7] .......................................... C07D 207/00
(52) U.S. Cl. ...................................................... 548/537
(58) Field of Search ......................................... 548/537

(56) References Cited

U.S. PATENT DOCUMENTS

| | | | |
|---|---|---|---|
| 5,273,995 A | 12/1993 | Roth | ........................... 514/422 |
| 5,385,929 A | 1/1995 | Bjorge et al. | |
| 6,528,660 B1 * | 3/2003 | Kumar et al. | ................ 548/537 |
| 6,613,916 B2 * | 9/2003 | Pflaum | ........................ 548/537 |

FOREIGN PATENT DOCUMENTS

| | | | |
|---|---|---|---|
| WO | WO 97/03958 | 7/1996 | .......... C07D/207/34 |
| WO | WO 97/03959 | 7/1996 | .......... C07D/207/34 |
| WO | WO 97/03960 | 7/1996 | .......... C07D/207/34 |
| WO | WO 00/71116 | 11/2000 | .......... A61K/31/40 |

OTHER PUBLICATIONS

Baumann et al, The Convergent Synthesis of CI–981, an Optically Active, Highly Potent, Tissue Selective Inhibitor of HMG–CoA Reductase, Apr. 21, 1992.
Database Chemabs 1998.

* cited by examiner

*Primary Examiner*—Rita Desai
*Assistant Examiner*—Robert Shiao
(74) *Attorney, Agent, or Firm*—Bromberg & Sunstein LLP

(57) ABSTRACT

Atorvastatin, the substance known by the chemical name [R-(R*,R*)]-2-(4-fluorophenyl)-$\beta,\delta$ dihydroxy-5-(1-methylethyl)-3-phenyl-4-[(phenylamino)carbonyl]-1H-pyrrole-1-heptanoic acid hemi calcium salt, is readily available in one of its crystalline forms as it is known from the prior art. The present invention relates to a novel process for preparing atorvastatin in an amorphous form by precipitating the atorvastatin using a solvent of a second type from a solution of atorvastatin which is provided with a solvent of a first type. This process is useful for the conversion of atorvastatin in a crystalline form into atorvastatin in an amorphous form.

16 Claims, 2 Drawing Sheets

PROCESS FOR THE PREPARATION OF AMORPHOUS ATORVASTATIN

Figure 1:
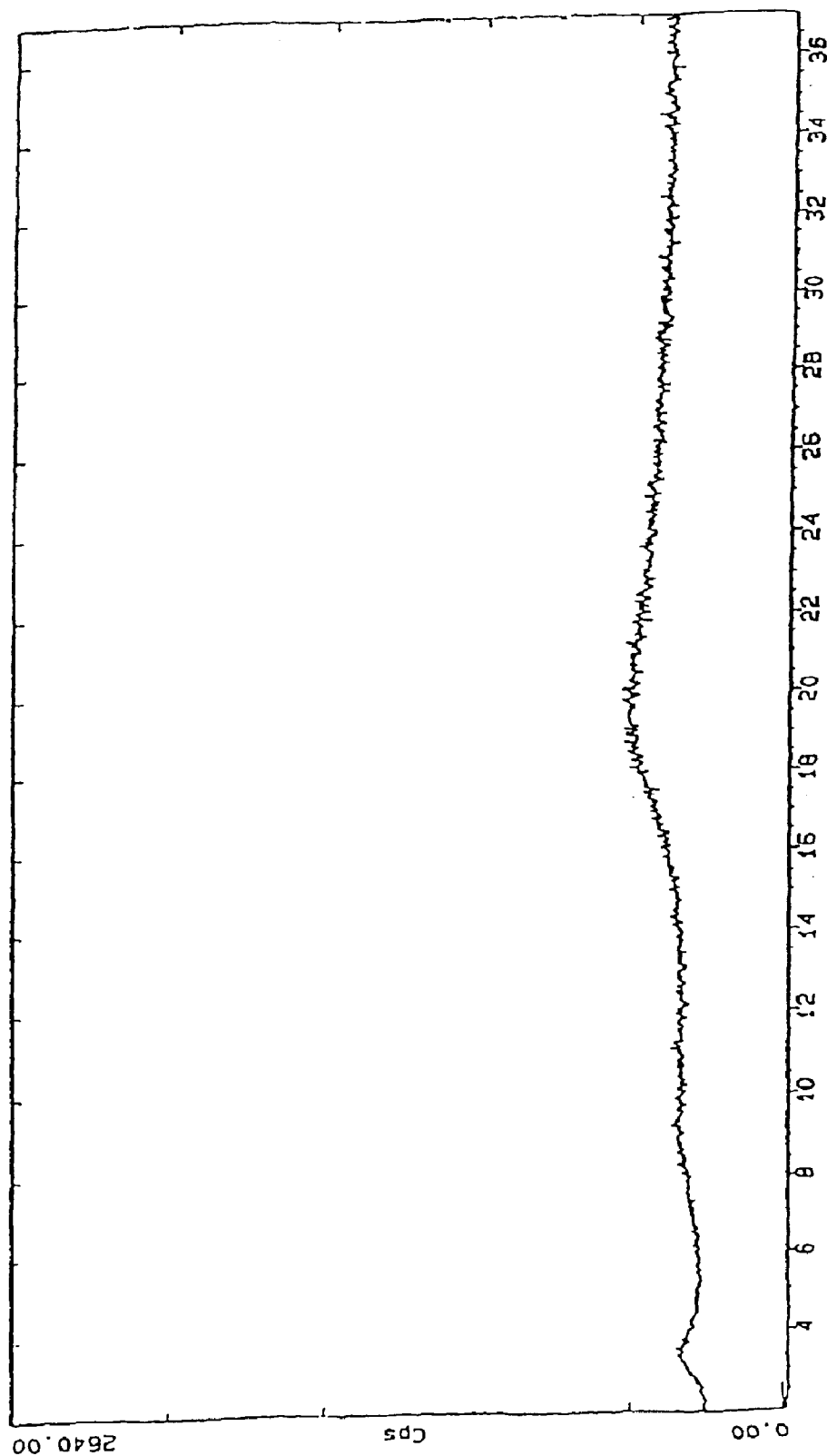

The present application is a continuation of U.S. patent application Ser. No. 10/149,348 filed Jun. 6 2002 now U.S. Pat. No. 6,613,916, which is based on International Application No. PCT/IB00/01797 filed Dec. 5, 2000, and Slovenia Patent Application No. P-9900271 filed Dec. 10, 1999. These applications are incorporated herein by reference.

The present invention relates to a novel process for the preparation of atorvastatin in an amorphous form.

Atorvastatin, the substance known by the chemical name [R-(R*,R*)]-2-(4-fluorophenyl)-β,δ-dihydroxy-5(1-methylethyl)-3-phenyl-4-[(phenylamino)carbonyl]-1H-pyrrole-1-heptanoic acid hemi calcium salt is known as HMG-CoA reductase inhibitor and is used as an antihypercholesterolemic agent. Processes for the preparation of atorvastatin and key intermediates are disclosed in the U.S. Pat. Nos.: 5,003,080; 5,097,045; 5,103,024; 5,124,482; 5,149,837; 5,155,251; 5,216,174; 5,245,047; 5,248,793; 5,280,126; 5,342,952; and 5,397,792. Atorvastatin is usually prepared as its calcium salt since it enables atorvastatin to be conveniently formulated in the pharmaceutical formulations, for example, in tablets, capsules, powders and the like for oral administration.

Atorvastatin can exist in an amorphous form or in one of the crystalline forms (Form I, Form II, Form III and Form IV), which are disclosed in the PCT patent applications WO-A-97/3958 and WO-A-97/3959. It is known that the amorphous forms in a number of pharmaceutical substances exhibit different dissolution characteristics and bioavailability patterns compared to the crystalline forms (Konno T., Chem Pharm Bull., 1990,38: 2003–2007). For some therapeutic indications the bioavailability is one of the key parameters determining the form of the substance to be used in a pharmaceutical formulation. Since processes for the crystallization and the preparation, respectively, of the amorphous substance are sometimes difficult to be performed, and as a product afford amorphous-crystalline mixtures, that is, a crystalline form instead of an amorphous form, there is a constant need for processes which enable the preparing of atorvastatin in an amorphous form without simultaneous formation of crystalline forms, or which will enable the conversion of the crystalline forms into the amorphous form.

Atorvastatin is the substance which is very slightly water-soluble, and it has been found that the crystalline forms are less readily soluble than the amorphous form which may cause problems in the bioavailability of atorvastatin in the body. It has been found that the is production of amorphous atorvastatin according to the previously disclosed processes was not consistently reproducible, therefore the process has been developed for converting the crystalline forms of atorvastatin (formed in the synthesis of atorvastatin) to the amorphous form. The process is described in the PCT patent application WO-A-97/3960 and comprises dissolving the crystalline form of atorvastatin in a non-hydroxylic solvent and after removal of the solvent affords amorphous atorvastatin. The preferred non-hydroxylic solvent is selected from the group consisting of tetrahydrofuran, and mixtures of tetrahydrofuran and toluene. The disadvantage of the above process is primarily the use of non-nature-friendly solvents. Furthermore, even after extensive and strict drying measures, the amorphous atorvastatin product still contains amounts of the non-hydroxylic solvent.

It is an object of the present invention to provide an improved process for the preparation of atorvastatin in a more amorphous state compared to the above-mentioned processes of the prior art.

This and further objects are accomplished by the present invention.

The object of the present invention is achieved by a process for the preparation of atorvastatin in an amorphous form, which comprises:

a) providing a solution of atorvastatin in one or more solvents of a first type such that atorvastatin is freely soluble;

b) providing a mixture of said atorvastatin solution with one or more solvents of a second type, in which atorvastatin is insoluble or very slightly soluble, such that atorvastatin precipitates;

c) separating the precipitate formed in step (b) from the mixture of solvents.

Further objects can be achieved by preferred embodiments as set forth in the claims being dependent from claim 1.

In the following, the drawings will be briefly described.

FIG. 1: Diffractogram of amorphous atorvastatin prepared by a process according to the present invention.

Figure 2:
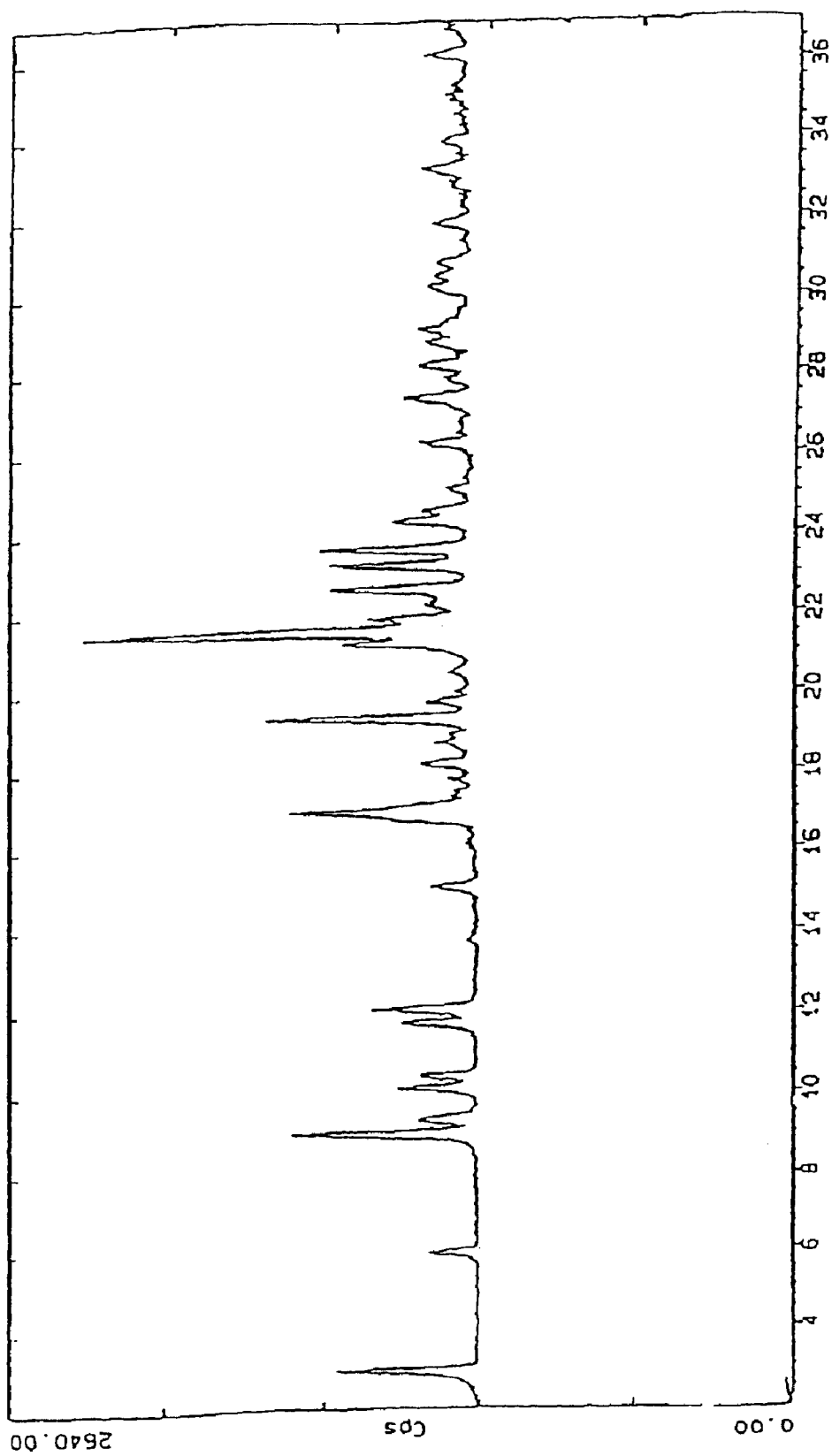

FIG. 2: Diffractogram of crystalline atorvastatin (Form I crystals).

X-ray diffraction measurements were carried out with an X-ray powder diffractometer (Siemens D-5000) using a Cu—$K_\alpha$ light source ($\lambda$=1.5406 Å, 20 mA) within 2 to 37° 2θ range with a 0.035° 2θ step and an integration time of 1 second/step. Variable slits were adjusted to 20 mm sample illumination, and entrance slit to 0.6 mm.

The features of the present invention will become more apparent from the following description of the inventive concept and the description of the preferred embodiments.

In the inventor's investigations, it was found that by means of combined steps of (i) providing a solution of atorvastatin and (ii) precipitating atorvastatin in respectively appropriate solvent media, amorphous atorvastatin can be obtained in an efficient manner at a high yield and in pure form with ease and with solvents which are cheap and environmentally less critical and less harmful to health than those required according to WO-A-97/3960.

In the first step of the process according to the present invention, a solution of atorvastatin is provided. Preferably, the solution used is obtained in the last step of the preparation of atorvastatin, or is obtained by dissolving crystalline atorvastatin or a mixture of crystalline and/or polycrystalline and amorphous atorvastatin, which is usually obtained by the preparation of solid atorvastatin, in one or more solvents of the first type such that atorvastatin is freely soluble (step a). The expression "freely soluble" means that atorvastatin can be fully dissolved in one or more solvents of the first type, i.e. without any remaining solid. More specifically, the amount of first type solvent required for solving 1 part of atorvastatin may be in the range of less than 1 part to 30 parts, and more preferably less than 1 part to 10 parts. One or more solvents means one solvent species or a mixture of solvent species of the first type.

For preferably achieving a fast precipitating of amorphous atorvastatin in step (b), the concentration of the solution of atorvastatin containing one or more solvents of the first type is preferably adjusted to a range of 0.1 to 150 g/l, and more preferably 4 to 100 g/l.

In the second step (step b), a mixture of the abovementioned atorvastatin solution with one or more solvents of the second type, in which atorvastatin is insoluble or very slightly soluble, is provided. The mixing step is carried out that, finally, atorvastatin precipitates. More specifically, the terms "insoluble" and "very slightly soluble" may be understood to mean that the amount of second type solvent required for solving 1 part of atorvastatin at room temperature and atmospheric pressure is in the range of 1.000 parts to 10.000 parts or more, and more preferably of 8.000 parts to 10.000 parts or more. One or more solvents means one solvent species or a mixture of solvent species of the second type.

The mixing in step (b) may be accomplished in two different embodiments. In a first embodiment, the mixture is provided by adding one or more solvents of the second type into the atorvastatin solution obtained in step (a). In a second, preferred embodiment, the mixture is provided by adding the atorvastatin solution of step (a) into one or more solvents of the second type. Both embodiments result in the precipitation of amorphous atorvastatin in a pure form.

In step (c) of the process according to the present invention, the precipitate of amorphous atorvastatin formed in step (b) is separated from the mixture of solvents used. The separation of atorvastatin may be accomplished by decanting, filtrating and similar processing methods for separating solids from liquids known from the prior art, or any combination of these separation methods.

Then, the amorphous atorvastatin product obtained may preferably be dried in a further step (d).

Step (a) of the process according to the present invention may be modified such that firstly either a solution of atorvastatin is provided in one or more solvents of the first type or crystalline atorvastatin is dissolved in one or more solvents of the first type, and secondly a mixture of this solution is provided with one or more solvents of the second type with the proviso that atorvastatin is still soluble, i.e. does not yet precipitate, in this mixture of solvents.

Moreover, the atorvastatin solution may advantageously concentrated before the second type solvent is added to obtain a more concentrated solution of atorvastatin, which is useful for requiring only a small amount of the one or more solvents of the second type and for obtaining atorvastatin at a high yield by adding.

In a preferred embodiment for the processing of step (b), a first mixture is provided by adding one or more solvents of the second type into the solution of step (a) such that atorvastatin is still soluble, i.e. does not yet precipitate, followed by adding additional amounts of one or more solvents of the second type such that atorvastatin precipitates. To decrease the tendency of crystallization of atorvastatin, a fast addition in the second step (b) is preferably carried out, e.g. during continuous stirring of the solution.

The one or more solvents of the first type used in the process of the present invention are selected from the group of solvents, in which atorvastatin is soluble or good soluble. Preferred examples of solvents of the first type are polar solvents such as low molecular alcohols, e.g. methanol and ethanol, or polar aprotic solvents such as ketones, e.g. acetone, ethyl methyl ketone, diethyl ketone, diisopropyl ketone, and the like, esters, e.g. ethyl acetate, n-butyl acetate, isobutyl acetate, and the like, chlorinated solvents, e.g. chloroform, methylene chloride, and the like, dimethyl formamide, dimethyl sulfoxide, tetrahydrofuran or the like. Particularly preferred solvents of the first type are selected from the group of solvents consisting of methanol, ethanol and acetone, which can easily be removed in the drying step and are less harmful or environmentally hazardous than the conventionally used solvents.

The one or more solvents of the second type used in the process of the present invention are selected from the group of solvents, in which atorvastatin is insoluble or very slightly soluble. The low solubility of atorvastatin in this solvent is preferably at most I part of atorvastatin/from 1.000 to 10.000 or more parts of second type solvent and more preferably at most 1 part of atorvastatin/from 8.000 to 10.000 or more parts of second type solvent. Preferred examples of solvents of the second type are solvents such as ethers, aliphatic compounds or the like. Particularly preferred solvents of the second type are selected from the group of solvents consisting of diethyl ether, diisopropyl ether, pentane, hexane, and the like, in which atorvastatin is very slightly soluble or insoluble, but which can easily be removed in the drying step and which are less harmful or environmentally hazardous than the conventionally used solvents.

For preferably achieving a suitable precipitation, it is preferred that the total amount of the one or more solvents of the second type added to the solution of atorvastatin during the whole process of the present invention is at least 4 times higher, more preferably 5 to 12 times higher, than the total amount of the solvents of the first type added during the whole process. With such an excess of the one or more solvents of the second type over the one or more solvents of the first type the solubility of atorvastatin in the mixture of solvents is low enough that the tendency of atorvastatin to crystallize is reduced and the yield of amorphous atorvastatin is excellent.

In view of this process according to the present invention, it is possible to prepare atorvastatin essentially, and more advantageously completely in an amorphous state.

The present invention is illustrated but in no way limited by the following examples.

EXAMPLES

Example 1

1.5 g of atorvastatin (crystalline Form I) were dissolved in 37.5 ml of methanol, concentrated to 10 ml on a rotary evaporator and to this solution were added 100 ml of ether. The formed precipitate was filtered and dried on a rotary evaporator (50° C. 100 mbar, 24 h). Yield: 1.3 g of the colourless precipitate of amorphous atorvastatin.

Example 2

1.5 g of atorvastatin (crystalline Form I) were dissolved in 300 ml of ethanol, concentrated to 30 ml on a rotary evaporator and to this solution were added 300 ml of ether. The formed precipitate was filtered and dried on a rotary evaporator (50° C. 100 mbar, 24 h). Yield: 1.3 g of the colourless precipitate of amorphous atorvastatin.

Example 3

1.5 g of atorvastatin (crystalline Form I) were dissolved in 136 ml of acetone, concentrated to 30 ml on a rotary evaporator and to this solution were added 300 ml of ether. The formed precipitate was filtered and dried on a rotary evaporator (50° C. 100 mbar, 24 h). Yield: 1.3 g of the colourless precipitate of amorphous atorvastatin.

Example 4

10 g of atorvastatin (crystalline Form I) were dissolved in 130 ml of methanol, concentrated to 30 ml on a rotary evaporator and to this solution were added 30 ml of ether. The resulting mixture was added to 1.300 ml of ether while stirring. The formed precipitate was filtered and dried on a rotary evaporator (50° C., 100 mbar, 24 h). Yield: 8.8 g of the colourless precipitate of amorphous atorvastatin, however the obtained amorphous atorvastatin had ca. 110% higher content than the starting crystalline substance.

Example 5

90 g of atorvastatin (crystalline Form I) were dissolved in 1 liter of methanol, filtered and concentrated to 300 ml on a rotary evaporator. To this solution were added 500 ml of ether and while stirring it was added to 2.5 liters of ether. The formed precipitate was filtered and dried on a rotary evaporator (50° C., 100 mbar, 24 h). Yield: 87 g of the colourless precipitate of amorphous atorvastatin.

Atorvastatin, the substance known by the chemical name [R-(R*,R*)]-2-(4-fluorophenyl)-β,δ-dihydroxy-5(1-methylethyl)-3-phenyl-4-[(phenylamino)carbonyl]-1H-pyrrole-1-heptanoic acid hemi calcium salt, is readily available in one of its crystalline forms as it is known from the prior art.

The present invention relates to a novel process for preparing atorvastatin in an amorphous form by precipitating the atorvastatin using a solvent of a second type from a solution of atorvastatin which is provided with a solvent of a first type. This process is useful for the conversion of atorvastatin in a crystalline form into atorvastatin in an amorphous form.

What is claimed is:

1. A process for the preparation of atorvastatin in an amorphous form, which comprises:
   a) providing a solution of atorvastatin in one or more solvents of a first type such that atorvastatin is freely soluble;
   b) providing a mixture of said atorvastatin solution with one or more solvents of a second type, in which atorvastatin is insoluble or very slightly soluble, such that atorvastatin precipitates;
   c) separating the precipitate formed in step (b) from the mixture of solvents;
   wherein the solvent of the first type is a chlorinated solvent selected from the group consisting of chloroform and methylene chloride, a polar solvent selected from the group consisting of dimethyl formamide and dimethyl sulfoxide, or a mixture thereof and wherein the solvent of the second type comprises at least one solvent selected from the group consisting of ether solvents and aliphatic solvents.

2. A process according to claim 1, further comprising: d) drying the amorphous product obtained.

3. A process according to claim 1, wherein said mixture in step (b) is provided by adding one or more solvents of the second type into the atorvastatin solution.

4. A process according to claim 1, wherein the mixture in step (b) is provided by adding the atorvastatin solution into one or more solvents of the second type.

5. A process according to claim 1, wherein step (a) comprises the two steps:
   i) providing a solution of atorvastatin in one or more solvents of the first type, and
   ii) providing a mixture by adding one or more solvents of the second type into said solution of atorvastatin such that atorvastatin is still soluble in said mixture of solvents.

6. A process according to claim 1, wherein step (b) comprises the following two steps:
   i) providing a first mixture by adding one or more solvents of the second type into the solution of step (a) such that atorvastatin is still soluble, and
   ii) additionally adding one or more solvents of the second type such that atorvastatin precipitates.

7. A process according to claim 1, wherein the concentration of atorvastatin in said one or more solvents of the first type is adjusted to a range of 0.1 to 150 g/l.

8. A process according to claim 1, wherein step (a) comprises the step of concentrating the atorvastatin solution to obtain a more concentrated solution.

9. A process according to claim 1, wherein said one or more solvents of the first type comprises at least one solvent selected from the group consisting of polar or chlorinated solvents.

10. A process according to claim 9, wherein said one or more solvents of the first type comprises at least one low molecular alcohol.

11. A process according to claim 10, wherein said low molecular alcohol is methanol and/or ethanol.

12. A process according to claim 9, wherein said polar solvent is an aprotic solvent.

13. A process according to claim 12, wherein said polar aprotic solvent is acetone.

14. A process according to claim 1, wherein said solvent of the second type is diethyl ether.

15. A process according to claim 1, wherein the total amount of said solvents of the second type is at least 4 times higher than the total amount of said solvents of the first type.

16. A process according to claim 15, wherein the total amount of said solvents of the second type is 5 to 12 times higher than the total amount of said solvents of the first type.

* * * * *